(12) United States Patent
Lin et al.

(10) Patent No.: US 12,244,966 B2
(45) Date of Patent: Mar. 4, 2025

(54) PROVIDING TEMPLATE ROOMS WITHIN A VIRTUAL CONFERENCING SYSTEM

(71) Applicant: Snap Inc., Santa Monica, CA (US)

(72) Inventors: Andrew Cheng-min Lin, Long Island, NY (US); Walton Lin, Chatham, NJ (US)

(73) Assignee: Snap Inc., Santa Monica, CA (US)

( * ) Notice: Subject to any disclaimer, the term of this patent is extended or adjusted under 35 U.S.C. 154(b) by 35 days.

(21) Appl. No.: 17/956,549

(22) Filed: Sep. 29, 2022

(65) Prior Publication Data

US 2023/0094963 A1 Mar. 30, 2023

Related U.S. Application Data

(60) Provisional application No. 63/261,872, filed on Sep. 30, 2021.

(51) Int. Cl.
| | |
|---|---|
| *H04N 7/15* | (2006.01) |
| *C12N 15/115* | (2010.01) |
| *C12Q 1/6848* | (2018.01) |
| *C12Q 1/686* | (2018.01) |
| *G06T 19/20* | (2011.01) |
| *H04N 7/14* | (2006.01) |

(52) U.S. Cl.
CPC ........... *H04N 7/157* (2013.01); *C12N 15/115* (2013.01); *C12Q 1/6848* (2013.01); *C12Q 1/686* (2013.01); *G06T 19/20* (2013.01); *H04N 7/147* (2013.01); *H04N 7/152* (2013.01); *C12N 2310/16* (2013.01); *G06T 2200/24* (2013.01)

(58) Field of Classification Search
CPC ......... H04N 7/157; H04N 7/147; H04N 7/152
See application file for complete search history.

(56) References Cited

U.S. PATENT DOCUMENTS

| | | |
|---|---|---|
| 6,330,022 B1 | 12/2001 | Seligmann |
| 6,414,707 B1 | 7/2002 | Agraharam et al. |
| 7,362,349 B2 | 4/2008 | Nelson et al. |
| 8,345,082 B2 | 1/2013 | Tysso |
| 8,624,955 B2 | 1/2014 | Watson et al. |
| 8,875,031 B2 | 10/2014 | Periyannan et al. |

(Continued)

FOREIGN PATENT DOCUMENTS

| | | |
|---|---|---|
| CN | 107925743 | 4/2018 |
| EP | 1381237 | 1/2004 |

(Continued)

*Primary Examiner* — Amal S Zenati
(74) *Attorney, Agent, or Firm* — Schwegman Lundberg & Woessner, P.A.

(57) ABSTRACT

Aspects of the present disclosure involve a system comprising a computer-readable storage medium storing a program and method for providing template rooms within a virtual conferencing system. The program and method provide for providing an interface to configure a template room for virtual conferencing; receiving, via the interface, an indication of user input specifying a configuration for the template room; accessing a data file comprising values for generating plural rooms based on the configuration for the template room; and providing, based on the configuration for the template room and on the data file, for virtual conferencing between plural participants across the plural rooms.

19 Claims, 10 Drawing Sheets

(56) References Cited

U.S. PATENT DOCUMENTS

| | | |
|---|---|---|
| 8,885,013 B2 | 11/2014 | Periyannan et al. |
| 9,007,427 B2 | 4/2015 | Hoover et al. |
| 9,035,997 B2 | 5/2015 | Periyannan et al. |
| 9,041,765 B2 | 5/2015 | Periyannan et al. |
| 9,307,203 B2 | 4/2016 | Kleiner et al. |
| 9,374,233 B2 | 6/2016 | Narayanan |
| 9,392,225 B2 | 7/2016 | Eisenberg |
| 9,419,810 B2 | 8/2016 | Jones et al. |
| 9,438,859 B2 | 9/2016 | Kleiner et al. |
| 9,497,416 B2 | 11/2016 | Su |
| 9,521,170 B2 | 12/2016 | Bader-Natal et al. |
| 9,532,002 B2 | 12/2016 | Glass et al. |
| 9,674,244 B2 | 6/2017 | Katzman et al. |
| 9,900,554 B2 | 2/2018 | Ursin et al. |
| 9,961,119 B2 | 5/2018 | Bader-Natal et al. |
| 10,284,815 B2 | 5/2019 | Nagpal et al. |
| 10,567,448 B2 | 2/2020 | Bader-Natal et al. |
| 10,666,696 B2 | 5/2020 | Bader-Natal et al. |
| 10,735,690 B2 | 8/2020 | Nagpal et al. |
| 10,979,671 B1 | 4/2021 | Mcelroy |
| 10,992,907 B1 | 4/2021 | Bran |
| 11,362,848 B1 | 6/2022 | Lin et al. |
| 11,381,411 B1 | 7/2022 | Gale et al. |
| 11,445,149 B2 | 9/2022 | Bran |
| 11,489,684 B2 | 11/2022 | Lin et al. |
| 2002/0071026 A1 | 6/2002 | Agraharam et al. |
| 2004/0008249 A1 | 1/2004 | Nelson et al. |
| 2004/0008635 A1 | 1/2004 | Nelson et al. |
| 2010/0171807 A1 | 7/2010 | Tysso |
| 2011/0271208 A1 | 11/2011 | Jones et al. |
| 2011/0279634 A1 | 11/2011 | Periyannan et al. |
| 2011/0279637 A1 | 11/2011 | Periyannan et al. |
| 2011/0279638 A1 | 11/2011 | Periyannan et al. |
| 2011/0279639 A1 | 11/2011 | Anand et al. |
| 2012/0062689 A1 | 3/2012 | Sai et al. |
| 2012/0254858 A1* | 10/2012 | Moyers ............ H04L 12/1818 717/177 |
| 2012/0306992 A1 | 12/2012 | Watson et al. |
| 2013/0155169 A1 | 6/2013 | Hoover et al. |
| 2014/0085406 A1 | 3/2014 | Narayanan |
| 2014/0267550 A1* | 9/2014 | Nimri ................ H04N 7/152 348/14.09 |
| 2015/0103137 A1 | 4/2015 | Eisenberg et al. |
| 2015/0271447 A1 | 9/2015 | Glass et al. |
| 2015/0271448 A1 | 9/2015 | Kleiner et al. |
| 2015/0304366 A1 | 10/2015 | Bader-Natal et al. |
| 2015/0304607 A1 | 10/2015 | Bader-Natal et al. |
| 2016/0072862 A1 | 3/2016 | Bader-Natal et al. |
| 2016/0073056 A1 | 3/2016 | Katzman et al. |
| 2016/0073058 A1 | 3/2016 | Bader-Natal et al. |
| 2016/0073059 A1* | 3/2016 | Bader-Natal ........... H04N 7/148 348/14.03 |
| 2016/0173826 A1 | 6/2016 | Kleiner et al. |
| 2017/0070706 A1 | 3/2017 | Ursin et al. |
| 2017/0093933 A1 | 3/2017 | Bader-Natal et al. |
| 2018/0184047 A1 | 6/2018 | Simonsen et al. |
| 2018/0227337 A1 | 8/2018 | Bader-Natal et al. |
| 2019/0037171 A1 | 1/2019 | Nagpal et al. |
| 2019/0260964 A1 | 8/2019 | Nagpal et al. |
| 2021/0352120 A1 | 11/2021 | Masi et al. |
| 2021/0392294 A1 | 12/2021 | Bran |
| 2022/0321369 A1 | 10/2022 | Lin et al. |
| 2022/0321371 A1 | 10/2022 | Lin et al. |
| 2022/0321372 A1 | 10/2022 | Cho et al. |
| 2022/0321373 A1 | 10/2022 | Lin et al. |
| 2022/0321374 A1 | 10/2022 | Lin et al. |
| 2022/0321375 A1 | 10/2022 | Lin et al. |
| 2022/0321376 A1 | 10/2022 | Lin et al. |
| 2022/0321613 A1 | 10/2022 | Lin et al. |
| 2022/0321617 A1 | 10/2022 | Gale et al. |
| 2022/0321832 A1 | 10/2022 | Lin et al. |
| 2022/0321833 A1 | 10/2022 | Lin et al. |
| 2022/0353473 A1 | 11/2022 | Springer |
| 2022/0353474 A1 | 11/2022 | Springer et al. |
| 2022/0385490 A1 | 12/2022 | Lin et al. |
| 2022/0407735 A1 | 12/2022 | Gale et al. |
| 2023/0032922 A1 | 2/2023 | Lin et al. |
| 2023/0095314 A1 | 3/2023 | Lin et al. |
| 2023/0096597 A1 | 3/2023 | Lin et al. |
| 2023/0101377 A1 | 3/2023 | Lin et al. |
| 2023/0101879 A1 | 3/2023 | Lin et al. |

FOREIGN PATENT DOCUMENTS

| | | |
|---|---|---|
| EP | 1468559 | 10/2004 |
| EP | 2569937 | 3/2013 |
| EP | 3311561 | 4/2018 |
| EP | 2569940 | 8/2019 |
| EP | 3135032 | 10/2021 |
| GB | 2463621 | 3/2010 |
| WO | 03063484 | 7/2003 |
| WO | 2011137281 | 11/2011 |
| WO | 2011143427 | 11/2011 |
| WO | 2011143440 | 11/2011 |
| WO | 2015164380 | 10/2015 |
| WO | 2016037084 | 3/2016 |
| WO | 2016203263 | 12/2016 |
| WO | 2017039746 | 3/2017 |
| WO | 2022140539 | 6/2022 |
| WO | 2022164555 | 8/2022 |
| WO | 2022212386 | 10/2022 |
| WO | 2022212391 | 10/2022 |
| WO | 2022231842 | 11/2022 |
| WO | 2022231857 | 11/2022 |

* cited by examiner

FIG. 4

PROVIDING TEMPLATE ROOMS WITHIN A VIRTUAL CONFERENCING SYSTEM

CROSS-REFERENCE TO RELATED APPLICATION

This patent application claims the benefit of U.S. Provisional Patent Application No. 63/261,872, filed Sep. 30, 2021, entitled "PROVIDING TEMPLATE ROOMS WITHIN A VIRTUAL CONFERENCING SYSTEM", which is incorporated by reference herein in its entirety.

TECHNICAL FIELD

The present disclosure relates generally to virtual conferencing systems, including providing template rooms within a virtual conferencing system.

BACKGROUND

A virtual conferencing system provides for the reception and transmission of audio and video data between devices, for communication between device users in real-time.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some nonlimiting examples are illustrated in the figures of the accompanying drawings in which:

FIG. 4 illustrates a virtual space design interface with interface elements for designing a virtual space, in accordance with some example embodiments.

DETAILED DESCRIPTION

A virtual conferencing system provides for the reception and transmission of audio and video data between devices, for communication between device users in real-time. A virtual conferencing system allows a user to design or select a virtual space with multiple rooms for real-time communication. Participants may switch between the different rooms of the virtual space, for example, to engage in different conversations, events, seminars, and the like. In some cases, a user designing a room (e.g., an administrator) may wish to generate multiple rooms that are similar to each other, without necessarily having to manually configure each room.

The disclosed embodiments provide for allowing a user (e.g., administrator) to generate multiple rooms based on a single template room and a data file. The virtual conference server system provides an interface to configure a template room for virtual conferencing. The user may initially configure a template room via the interface. The user may then create or otherwise edit a data file with values for generating a plurality of rooms (e.g., tens of rooms, hundreds of rooms) based on the template room. The data file may include user-entered values for supplementing or otherwise customizing the template room, such that the multiple rooms vary in some aspects.

By virtue of allowing a user to define a template room and create a data file in this manner, it is possible for the user to create multiple rooms automatically in a batched fashion. In addition, the configuration of the multiple room may be more consistent across the virtual space. Without allowing the user (e.g., administrator) to configure generate multiple rooms via the data file, the user may be required to perform redundant actions (e.g., copying and pasting) to manually create each room. The virtual conferencing system facilitates creation of virtual conferencing environments, thereby saving time for the user, and reducing computational resources/processing power for the virtual conferencing system.

Figure 1:
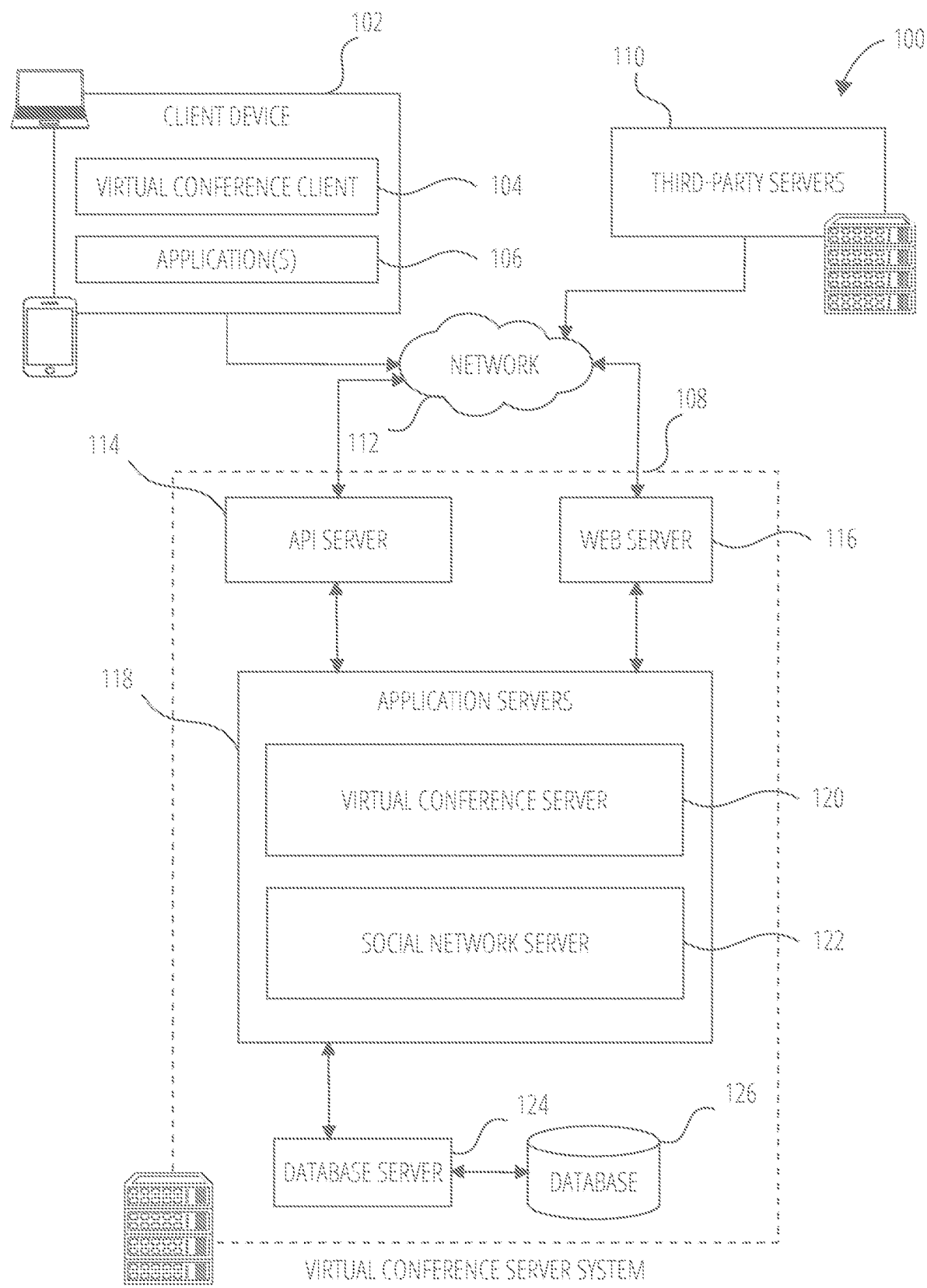
FIG. 1 is a diagrammatic representation of a networked environment in which the present disclosure may be deployed, in accordance with some examples.

FIG. 1 is a block diagram showing an example virtual conferencing system 100 for exchanging data over a network. The virtual conferencing system 100 includes multiple instances of a client device 102, each of which hosts a number of applications, including a virtual conference client 104 and other application(s) 106. Each virtual conference client 104 is communicatively coupled to other instances of the virtual conference client 104 (e.g., hosted on respective other client devices 102), a virtual conference server system 108 and third-party servers 110 via a network 112 (e.g., the Internet). A virtual conference client 104 can also communicate with locally-hosted applications 106 using Applications Program Interfaces (APIs).

The virtual conferencing system 100 provides for the reception and transmission of audio, video, image, text and/or other signals by user devices (e.g., at different locations), for communication between users in real-time. In some cases, two users may utilize virtual conferencing to communicate with each other in one-to-one communication at their respective devices. In other cases, multiway virtual conferencing may be utilized by more than two users to participate in a real-time, group conversation. Thus, multiple client devices 102 may participate in virtual conferencing, for example, with the client devices 102 participating in a group conversation in which audio-video content streams and/or message content (e.g., text, images) are transmitted between the participant devices.

A virtual conference client 104 is able to communicate and exchange data with other virtual conference clients 104 and with the virtual conference server system 108 via the network 112. The data exchanged between virtual conference clients 104, and between a virtual conference client 104 and the virtual conference server system 108, includes functions (e.g., commands to invoke functions) as well as payload data (e.g., video, audio, other multimedia data, text).

The virtual conference server system 108 provides server-side functionality via the network 112 to a particular virtual conference client 104. For example, with respect to transmitting audio and/or video streams, the virtual conference client 104 (e.g., installed on a first client device 102) may facilitate in transmitting streaming content to the virtual conference server system 108 for subsequent receipt by other participant devices (e.g., one or more second client devices 102) running respective instances of the virtual conference client 104.

The streaming content can correspond to audio and/or video content captured by sensors (e.g., microphones, video cameras) on the client devices 102, for example, corresponding to real-time video and/or audio capture of the users (e.g., faces) and/or other sights and sounds captured by the respective device. The streaming content may be supplemented with other audio/visual data (e.g., animations, overlays, emoticons and the like) and/or message content (e.g., text, stickers, emojis, other image/video data), for example, in conjunction with extension applications and/or widgets associated with the virtual conference client 104.

While certain functions of the virtual conferencing system 100 are described herein as being performed by either a virtual conference client 104 or by the virtual conference server system 108, the location of certain functionality either within the virtual conference client 104 or the virtual conference server system 108 may be a design choice. For example, it may be technically preferable to initially deploy certain technology and functionality within the virtual conference server system 108 but to later migrate this technology and functionality to the virtual conference client 104 where a client device 102 has sufficient processing capacity.

The virtual conference server system 108 supports various services and operations that are provided to the virtual conference client 104. Such operations include transmitting data to, receiving data from, and processing data generated by the virtual conference client 104. This data may include the above-mentioned streaming content and/or message content, client device information, and social network information, as examples. Data exchanges within the virtual conferencing system 100 are invoked and controlled through functions available via user interfaces (UIs) of the virtual conference client 104.

Turning now specifically to the virtual conference server system 108, an Application Program Interface (API) server 114 is coupled to, and provides a programmatic interface to, application servers 118. The application servers 118 are communicatively coupled to a database server 124, which facilitates access to a database 126 that stores data associated with virtual conference content processed by the application servers 118. Similarly, a web server 116 is coupled to the application servers 118, and provides web-based interfaces to the application servers 118. To this end, the web server 116 processes incoming network requests over the Hypertext Transfer Protocol (HTTP) and several other related protocols.

The Application Program Interface (API) server 114 receives and transmits virtual conference data (e.g., commands, audio/video payloads) between the client device 102 and the application servers 118. Specifically, the Application Program Interface (API) server 114 provides a set of interfaces (e.g., routines and protocols) that can be called or queried by the virtual conference client 104 in order to invoke functionality of the application servers 118. The Application Program Interface (API) server 114 exposes various functions supported by the application servers 118, including account registration, login functionality, the streaming of audio and/or video content, and/or the sending and retrieval of message content, via the application servers 118, from a particular virtual conference client 104 to another virtual conference client 104, the retrieval of a list of contacts of a user of a client device 102, the addition and deletion of users (e.g., contacts) to a user graph (e.g., a social graph), and opening an application event (e.g., relating to the virtual conference client 104).

The application servers 118 host a number of server applications and subsystems, including for example a virtual conference server 120 and a social network server 122. The virtual conference server 120 implements a number of virtual conference processing technologies and functions, particularly related to the aggregation and other processing of content (e.g., streaming content) included in audio-video feeds received from multiple instances of the virtual conference client 104. Other processor and memory intensive processing of data may also be performed server-side by the virtual conference server 120, in view of the hardware requirements for such processing.

Figure 3:
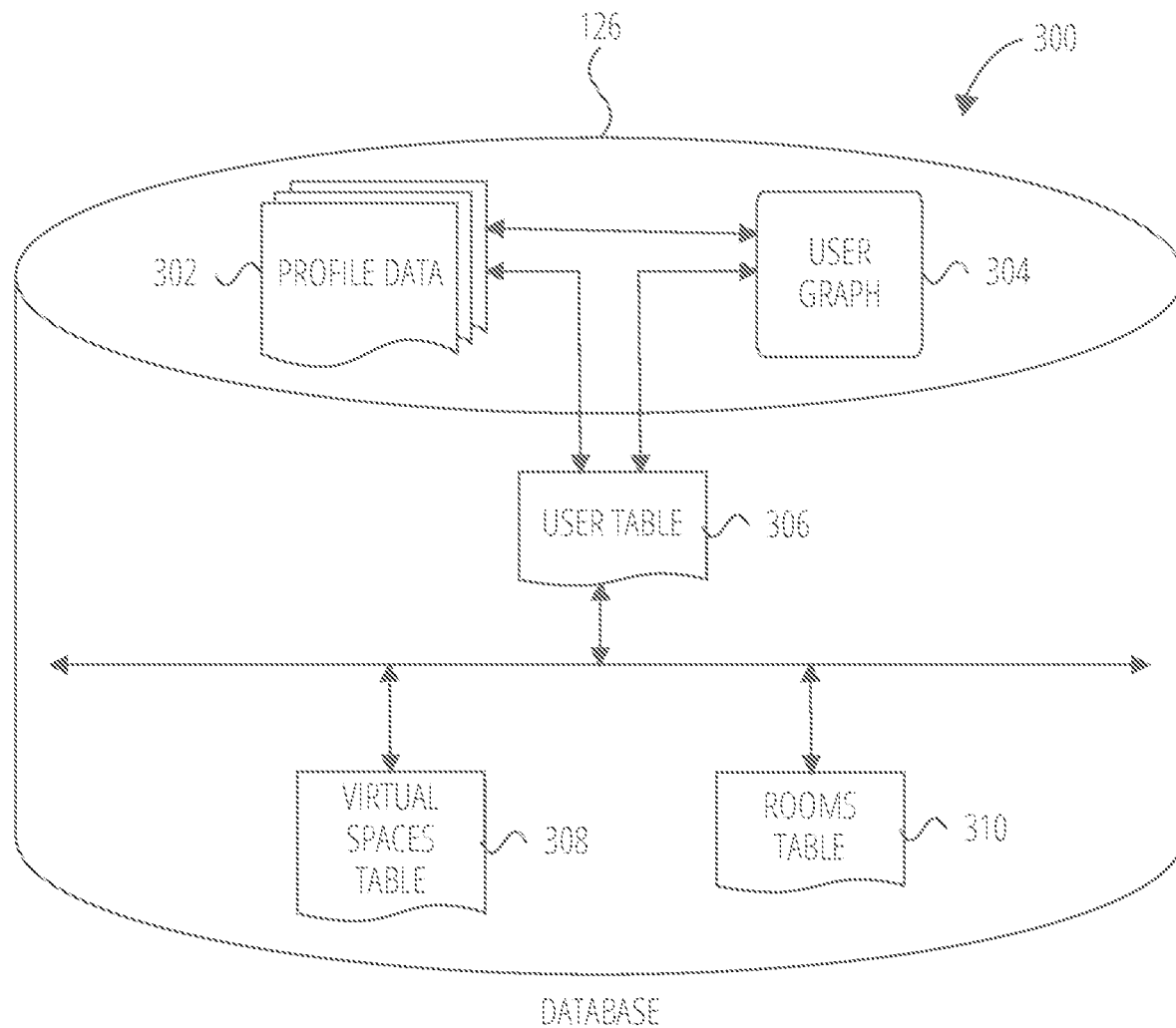
FIG. 3 is a diagrammatic representation of a data structure as maintained in a database, in accordance with some examples.

The social network server 122 supports various social networking functions and services and makes these functions and services available to the virtual conference server 120. To this end, the social network server 122 maintains and accesses a user graph 304 (as shown in FIG. 3) within the database 126. Examples of functions and services supported by the social network server 122 include the identification of other users of the virtual conferencing system 100 with which a particular user has relationships (e.g., contacts such as friends, colleagues, teachers, students, and the like).

In one or more embodiments, a user interacting via the virtual conference client 104 running on a first client device 102 may select and invite participant(s) to a virtual conference. For example, the participants may be selected from contacts maintained by the social network server 122. In another example, the participants may be selected from contacts included within a contact address book stored in association with the first client device 102 (e.g., in local memory or in a cloud-based user account). In another example, the participants may be selected by the user manually entering email addresses and/or phone numbers of the participants.

The user at the first client device 102 may initiate the virtual conference by selecting an appropriate user interface element provided by the virtual conference client 104, thereby prompting the invited participants, at their respective devices (e.g., one or more second client devices 102), to accept or decline participation in the virtual conference. When the participant(s) have accepted the invitation (e.g., via the prompt), the virtual conference server system 108 may perform an initialization procedure in which session information is published between the participant client devices 102, including the user who provided the invite. Each of the participant client devices 102 may provide respective session information to the virtual conference server system 108, which in turn publishes the session information to the other participant client devices 102. The session information for each client device 102 may include content stream(s) and/or message content that is made available by the client device 102, together with respective identifiers for the content stream(s) and/or message content.

As described below with respect to FIG. 2, the virtual conference may correspond to a virtual space which includes one or more rooms (e.g., virtual rooms). The virtual space and its corresponding rooms may have been created at least in part by the inviting user and/or by other users. In this manner, an end user may act as an administrator, who creates their own virtual spaces with rooms, and/or designs a virtual space based on preset available rooms.

Figure 2:
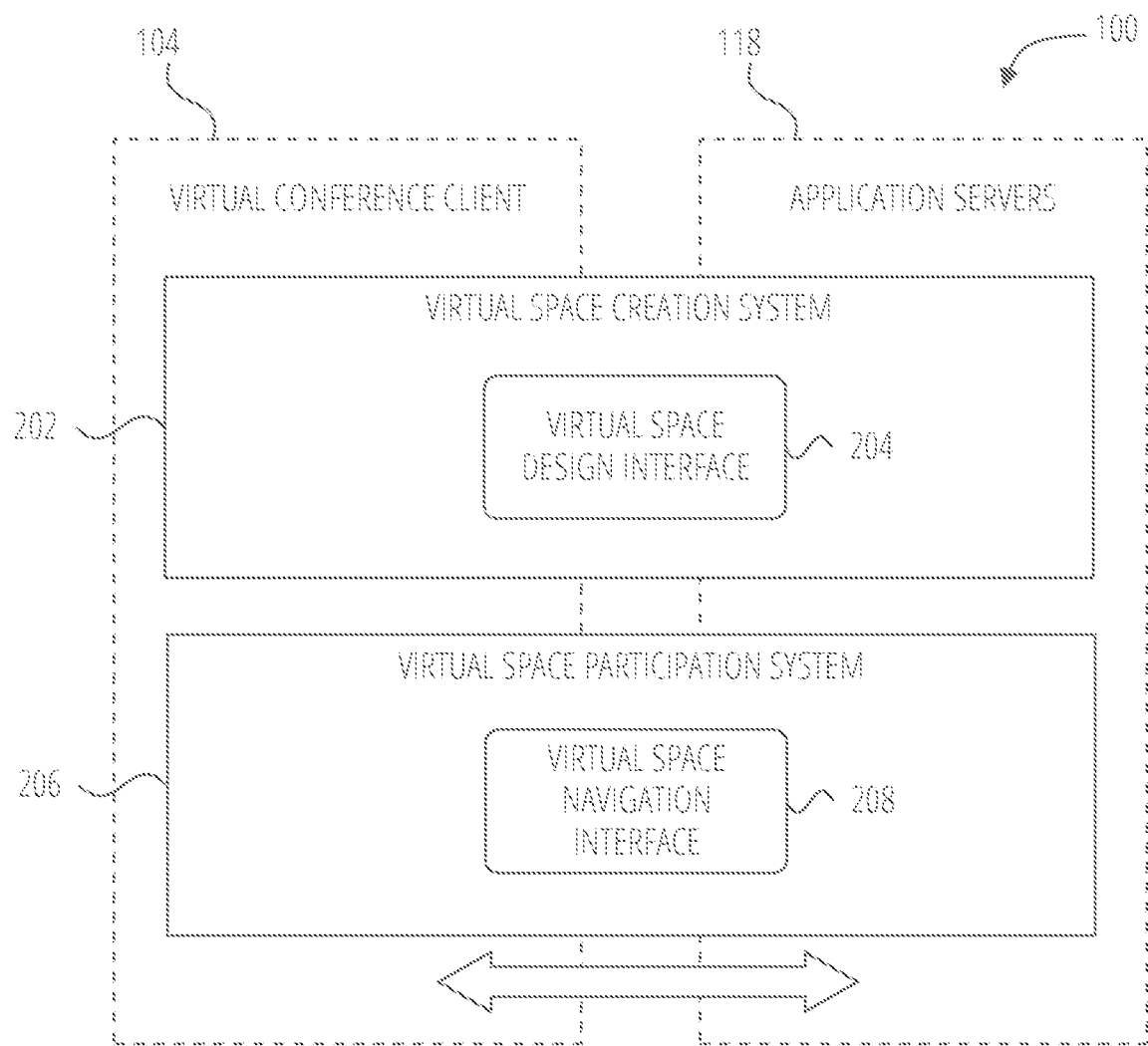
FIG. 2 is a diagrammatic representation of a virtual conferencing system, in accordance with some examples, that has both client-side and server-side functionality.

FIG. 2 is a block diagram illustrating further details regarding the virtual conferencing system 100, according to some examples. Specifically, the virtual conferencing system 100 is shown to comprise the virtual conference client 104 and the application servers 118. The virtual conferencing system 100 embodies a number of subsystems, which are supported on the client-side by the virtual conference client 104 and on the server-side by the application servers 118. These subsystems include, for example, a virtual space creation system 202 which implements a virtual space design interface 204, and a virtual space participation system 206 which implements a virtual space navigation interface 208.

The virtual space creation system 202 provides for a user to design one or more virtual space(s) in which participants may engage in virtual conferencing. In one or more embodiments, a virtual space corresponds to an environment with one or more rooms configured to accommodate virtual conferencing.

The virtual space may be created and/or selected (e.g., from among a set of predefined virtual spaces with rooms) by an end user who wishes to invite other users for virtual conferencing. In addition, the individual rooms of a virtual space may be newly-created and/or selected (e.g., from among a set of predefined rooms) by the end user. In one or more embodiments, the virtual space creation system 202 includes a virtual space design interface 204, which is usable by the end user to design a virtual space, including creating and/or selecting rooms for including in the virtual space.

As discussed below with respect to FIG. 4, the virtual space design interface 204 enables an end user (e.g., acting as an administrator) to select and/or position multiple elements within in a room. Examples of elements include, but are not limited to, participant video elements (e.g., for displaying the respective video feeds of participants), chat interfaces (e.g., for participants to provide text-based messages, stickers and/or reactions within a room), breakout buttons (e.g., for shuffling from a first room to one or more second rooms), and/or other user-definable elements for performing certain actions (e.g., speaking into a virtual microphone, querying an administrator via a button, and the like).

The virtual space participation system 206 is configured to perform virtual conferencing among participants within a virtual space. The participants may include the end user (e.g., administrator) who created the virtual space, as well as those users who were invited to participate in virtual conferencing with respect to the virtual space created/selected by the end user. The virtual space participation system 206 includes a virtual space navigation interface 208 (e.g., discussed below with respect to FIG. 5) that allows participants to navigate between the rooms of a virtual space, and to participate in virtual conferencing with respect to the rooms.

In one or more embodiments, the virtual space creation system 202 and the virtual space participation system 206 provide for an end user (e.g., an administrator) to create different types of environments (e.g., virtual spaces with rooms) for virtual conferencing, and for participants to engage in virtual conferencing within such environments. Examples of such virtual conferencing include, but are not limited to: business meetings, seminars, presentations, classroom lectures, teacher office hours, concerts, reunions, virtual dinners, escape rooms, and the like.

FIG. 3 is a schematic diagram illustrating data structures 300, which may be stored in the database 126 of the virtual conference server system 108, according to certain examples. While the content of the database 126 is shown to comprise a number of tables, it will be appreciated that the data could be stored in other types of data structures (e.g., as an object-oriented database).

The database 126 includes profile data 302, a user graph 304 and a user table 306 relating to the users (participants) of the virtual conferencing system 100. The user table 306 stores user data, and is linked (e.g., referentially) to the user graph 304 and the profile data 302. Each user of the virtual conferencing system 100 is associated with a unique identifier (email address, telephone number, social network identifier, etc.).

The user graph 304 stores (e.g., in conjunction with the social network server 122) information regarding relationships and associations between users. Such relationships may be social, professional (e.g., work at a common corporation or organization) interested-based or activity-based, merely for example. As noted above, the user graph 304 may be maintained and accessed at least in part by the social network server 122.

The profile data 302 stores multiple types of profile data about a particular user. The profile data 302 may be selectively used and presented to other users of the virtual conferencing system 100, based on privacy settings specified by a particular user. The profile data 302 includes, for example, a user name, telephone number, email address, and/or settings (e.g., notification and privacy settings), as well as a user-selected avatar representation.

The database 126 further includes a virtual spaces table 308. As noted above, a virtual space corresponds to an environment with one or more rooms configured to accommodate virtual conferencing. A virtual space may be newly-created by a user, or may be included within one or more sets of public virtual spaces made available (e.g., by other users, system administrators, and the like) for virtual conferencing. The virtual spaces table 308 stores information representing the one or more sets of public virtual spaces, as well as any private virtual space(s) created by a user (e.g., in a case where the particular user did not make such virtual space(s) public).

In one or more embodiments, the virtual spaces table 308 stores associations between its virtual spaces and users (e.g., within the user table 306) who selected those virtual spaces. In this manner, it is possible for a particular user to have one or more virtual spaces associated therewith. Moreover, the database 126 includes a rooms table 310 which may be associated with the virtual spaces within the virtual spaces table 308. As noted above, a room may be newly-created by a user, or may be included within one or more sets (e.g., galleries) of public rooms made available for user selection. The rooms table 310 stores information representing the one or more sets of rooms, as well as any private room(s) created by the user (e.g., in a case where the particular user did not make such room(s) public). The stored information is usable by the virtual conferencing system 100 to create the corresponding rooms for use in a virtual space. In one or more embodiments, the stored information may further include recordings (e.g., audio and/or video recordings) of a particular virtual conference, for subsequent playback by corresponding participants.

Figure 4:
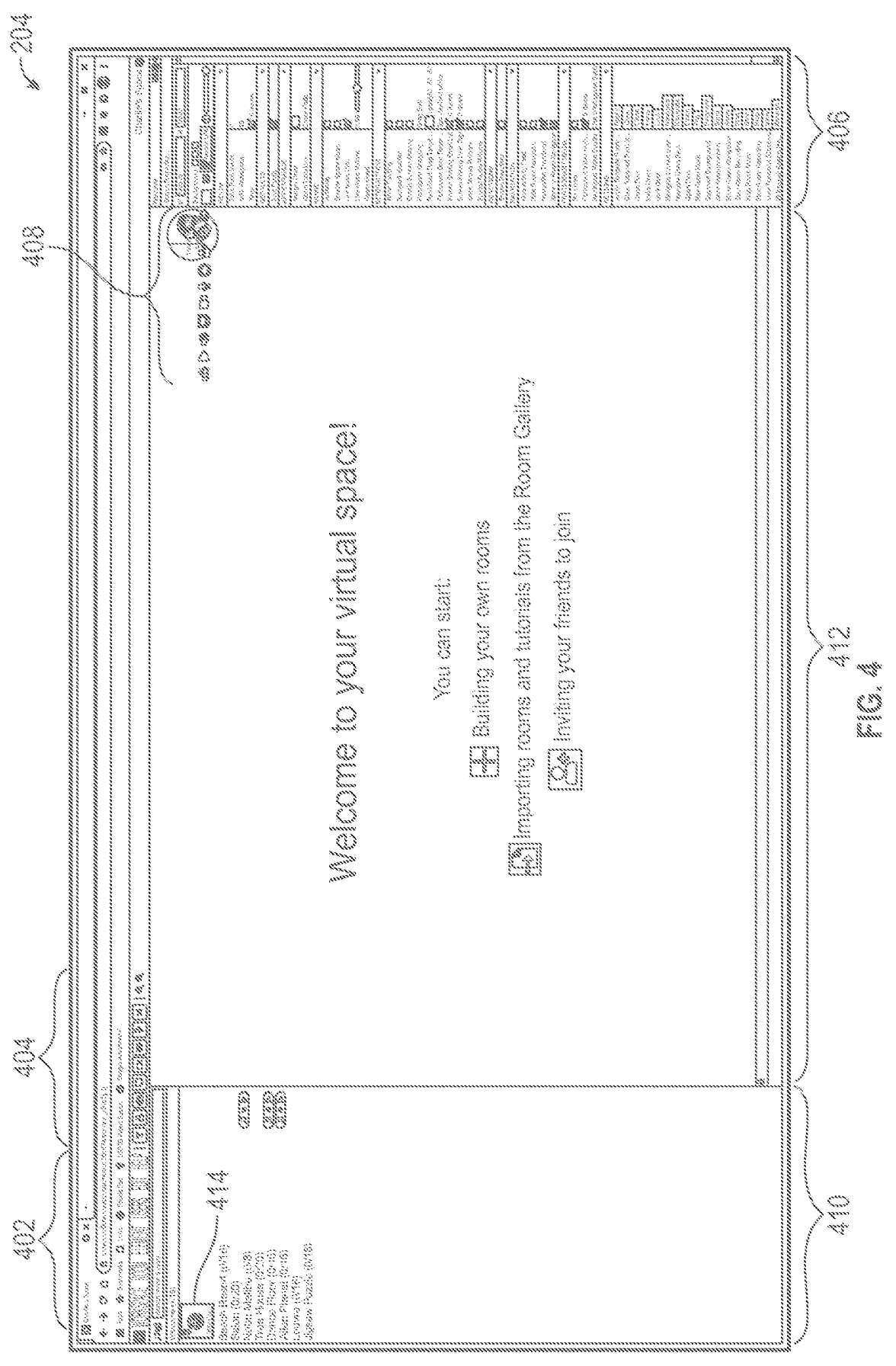

FIG. 4 illustrates a virtual space design interface 204 with interface elements for designing a virtual space, in accordance with some example embodiments. Designing the virtual space may include creation and/or selection of rooms for including in the virtual space. The virtual space design interface 204 includes a menu interface 402, a room elements interface 404, an element properties interface 406, a controls interface 408, a room list interface 410, a room canvas interface 412, and an administrator name 414. It is noted that elements 402-414 correspond to an example of interface elements for the virtual space design interface 204, and that additional, fewer and/or different interface elements may be used.

An administrator (e.g., corresponding to administrator name 414) may use the various interface elements to design a virtual space. In one or more embodiments, the menu interface 402 includes user-selectable categories (e.g., menu headings) relating to a virtual space (e.g., "workspace"), rooms within the virtual space, and/or elements within a room. For example, the workspace category is user-selectable for presenting options (e.g., via a drop-down list) to manage settings for the virtual space, manage invites for the virtual space, manage versions of a virtual space, publish the virtual space (e.g., for future use by users), manage virtual space publications, and/or to start/manage recordings (e.g., audio and/or video recordings) with respect to the virtual space.

The room category of the menu interface 402 is user-selectable for presenting options (e.g., via a drop-down list) to manage settings for a room within the virtual space, set a room background, set an order for the rooms listed in the room list interface 410, create a new room, import a room from a set of available rooms, remove a room, publish a room, manage room publications, and/or to start/manage recordings with respect to a room.

In addition, the element category is user-selectable for presenting options (e.g., via a drop-down list) to insert elements into a room, insert shapes into a room, foreground/background elements, arrange/position elements, and/or group elements. Examples of elements include, but are not limited to: an action button, analog clock, audience question board, backpack item, breakout button, chat, closed caption display, closed caption input, countdown, clock, digital clock, doorbell, double-sided image, feedback, image, multiuser video chat, music, participant audio mixer, participant count, participant video, picture strip, poll, random source, room preview, scheduled time, sound effect, stopwatch, take picture, text, timer, user search, video, waiting list, web media, website. Examples of shapes include, but are not limited to, a circle, rectangle and triangle.

The users category of the menu interface 402 is user-selectable for presenting options (e.g., via a drop-down list) to manage users/participants of the virtual space (e.g., adding tags for participants, so as to distinguish between roles such as an administrator or an attendee/participant). In addition, the edit category is user-selectable for performing edit operations (e.g., undo, redo, cut, copy, paste), and the help category is user-selectable for performing help operations (e.g., getting started, discord, live help, submitting feedback).

In one or more embodiments, the room elements interface 404 includes user-selectable icons for inserting elements (e.g., corresponding to a subset of those available via the above-mentioned element category) into a current room. For example, the elements may be added and/or positioned within the current room by selecting the element and dragging the selected element onto the room canvas interface 412, which represents the layout of the current room.

In one or more embodiments, the room elements interface 404 include icons including but not limited to: a text icon for adding text to a room; a participant video icon for adding a single participant video element (e.g., an interface element which is selectable by a single participant for displaying that participant's video feed) to a room; a multiuser video icon for adding a multiple participant video element (e.g., an interface element which is selectable by one or more participants for displaying the video feeds for those participants) to a room; a chat icon for adding a chat interface (e.g., for messaging using text, stickers, emojis, etc.) to a room; a video playback icon for adding a video playback element (e.g., screen) to a room for playback of a selected video; a background icon for selecting a background color/gradient, image or video to a room; an action icon for adding an action element (e.g., button) to a room for performing a user-defined action (e.g., speaking into a virtual microphone, querying an administrator via a button, and the like); and/or a breakout button for adding a breakout element (e.g., button) for shuffling selected participants between the current room and one or more other rooms.

In one or more embodiments, the element properties interface 406 include various fields for setting configuration properties for above-described room elements. For example, with respect to elements in general (e.g., text, single participant video element, multi participant video element, chat interface, video element, background image, action element, breakout button), the element properties interface 406 includes fields for setting the element title/name, opacity, gradient, style, layout, borders/corners, shadows, interaction (e.g., to what extent participant(s) may delete, modify, resize the element), filtering, full screen status, conditions, accessibility and actions for the element. For the single participant video element, the element properties interface 406 includes further fields for setting the manner in which users are placed into the single participant video element during virtual conferencing (e.g., automatically, manually by the participant and/or the administrator end user). In addition, for the chat interface, the element properties interface 406 includes further properties for setting who (e.g., administrator and/or participants) can provide chat input, and/or which types of input (e.g., text, stickers, emojis, etc.) are available. For the action element, the element properties interface 406 includes further properties for setting what type of action is to be performed in response to user selection of the action element (e.g., button). Moreover, for the breakout element, the element properties interface 406 includes further properties for selecting participants and/or breakout rooms.

In one or more embodiments, the element properties interface 406 includes fields for setting configuration properties for the room canvas interface 412. For example, the element properties interface 406 includes fields selecting a number of fake participants (e.g., simulated video feeds) in order to visualize multiple users, selecting music (e.g., background music), and/or selecting which reaction buttons are available for participants to indicate real-time reactions with respect to virtual conferencing within a room.

In one or more embodiments, the controls interface 408 includes user-selectable icons corresponding to controls (e.g., administrative controls) for the virtual space. For example, the controls interface 408 include icons including but not limited to: a director mode icon for toggling between a director mode for designing a room and a user mode for viewing the room within the virtual space design interface 204 (e.g., with the director mode including the room elements interface 404 and the element properties interface 406 while the user mode does not); a view icon for viewing the room within the virtual space navigation interface 208; a share screen icon (e.g., for collaborative design with other user(s) such as co-administrators); a microphone icon for enabling or disabling the microphone; a help icon (e.g., getting started, discord, live help, submitting feedback); an invite icon (e.g., for displaying an invite link for sending to participants to visit the virtual space); a settings icon (e.g., for selecting the end user's video and audio devices for the virtual conferencing, and for selecting a user avatar); and/or an exit icon for exiting the virtual space design interface 204.

In one or more embodiments, the room list interface 410 displays the list of rooms for the virtual space. Each listed room is user selectable to switch to edit (e.g., in director mode) and/or view (e.g., in user mode) the selected room. As noted above, the list of rooms may be modified (e.g., by adding, importing and/or removing rooms) via the options within the room category of the menu interface 402.

Figure 5:
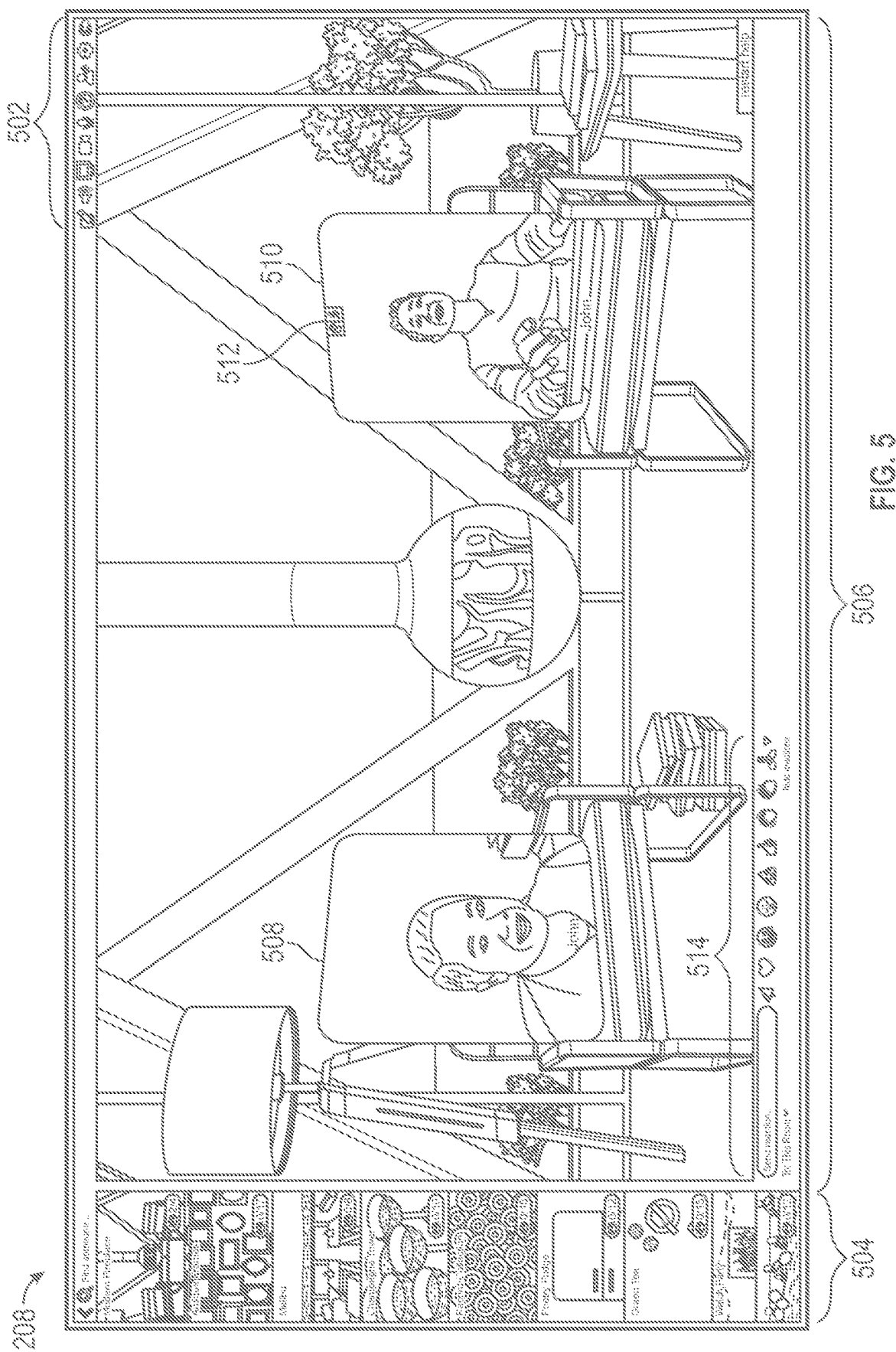
FIG. 5 illustrates a virtual space navigation interface with interface elements to navigate between the rooms of a virtual space and to participate in virtual conferencing with respect to the rooms, in accordance with some example embodiments.

FIG. 5 illustrates a virtual space navigation interface 208 with interface elements to navigate between the rooms of a virtual space and to participate in virtual conferencing with respect to the rooms, in accordance with some example embodiments. The virtual space navigation interface 208 includes a controls interface 502, a room list interface 504, a current room interface 506, a participant video element 508 and a participant video element 510. It is noted that elements 502-512 correspond to an example of interface elements for the virtual space navigation interface 208, and that additional, fewer and/or different interface elements may be used.

In one or more embodiments, the controls interface 502 includes user-selectable icons corresponding to controls (e.g., administrative controls) for the virtual space. For example, the controls interface 408 include icons including but not limited to: an edit icon for redirecting to the virtual space design interface 204 to edit the current room; a volume icon for adjusting a volume level for the current room; a share screen icon (e.g., for allowing others to view the room without necessarily joining the room); a microphone icon for muting and unmuting the microphone; a help icon (e.g., getting started, discord, live help, submitting feedback); an invite icon (e.g., for displaying an invite link for participants to visit the virtual space); a settings icon (e.g., for selecting the end user's video and audio devices for the virtual conferencing, and for selecting a user avatar); and/or an exit icon for exiting the virtual space design interface 204.

In one or more embodiments, the room list interface 504 displays the list of rooms for the virtual space. Each listed room is user selectable to switch to the selected room (e.g., for virtual conferencing). The selected room is presented as a current room within the current room interface 506. In this manner, a participant may navigate among the multiple rooms available within the virtual space. Alternatively or in addition, navigation between rooms is possible via a virtual space map interface (not shown) which depicts a map view of the virtual space (e.g., a floor plan) and its corresponding rooms, with each room being user selectable to navigate thereto. Alternatively or in addition, navigation between rooms is further possible by positioning a navigation button (not shown) within a room, where user selection of the button results in navigating to another room (e.g., a predefined room). As noted above, the virtual space design interface 204 allows for the design of a virtual space and its corresponding rooms. As such, navigation between rooms is based at least in part on the design of the virtual space (e.g., a virtual space may include one or more of the above-mentioned room list interface 504, the virtual space map/floor plan interface and/or the navigation button).

With respect to the current room interface 506, each participant is represented as a respective participant video element. As noted above, a participant video element corresponds to an interface element (e.g., a box) which is selectable by a single participant for displaying that participant's video feed. The example of FIG. 5 includes a first participant associated with the participant video element 508 and a second participant associated with the participant video element 510. In one or more embodiments, with respect to the perspective of the first participant, the participant video element 510 showing the feed of the second participant may include participant button(s) 512. For example, the participant button(s) 512 are selectable by the first participant so as to perform a predefined action (e.g., initiate a side conversation, designate the second participant to follow the first participant when the first participant moves rooms) with respect to the second participant.

While the example of FIG. 5 illustrates two participants, it is possible for the current room interface 506 to accommodate additional participants for virtual conferencing. The additional participants may be positioned (e.g., automatically and/or manually by dragging) based on the positioning of participant video elements (e.g., boxes) as designed by the virtual space design interface 204.

In one or more embodiments, the virtual space navigation interface 208 may vary based on whether a given participant is an administrator or another participant (e.g., an attendee). For example, some participant video elements may be designated (e.g., via the virtual space design interface 204) for administrators, while other participant video elements are designated for other participants. The virtual conference server system 108 is configured to distinguish between these administrator or other participant roles, for example, based on the above-described tags assigned to participants via the users category of the menu interface 402 provided by the virtual space design interface 204.

Figure 6:
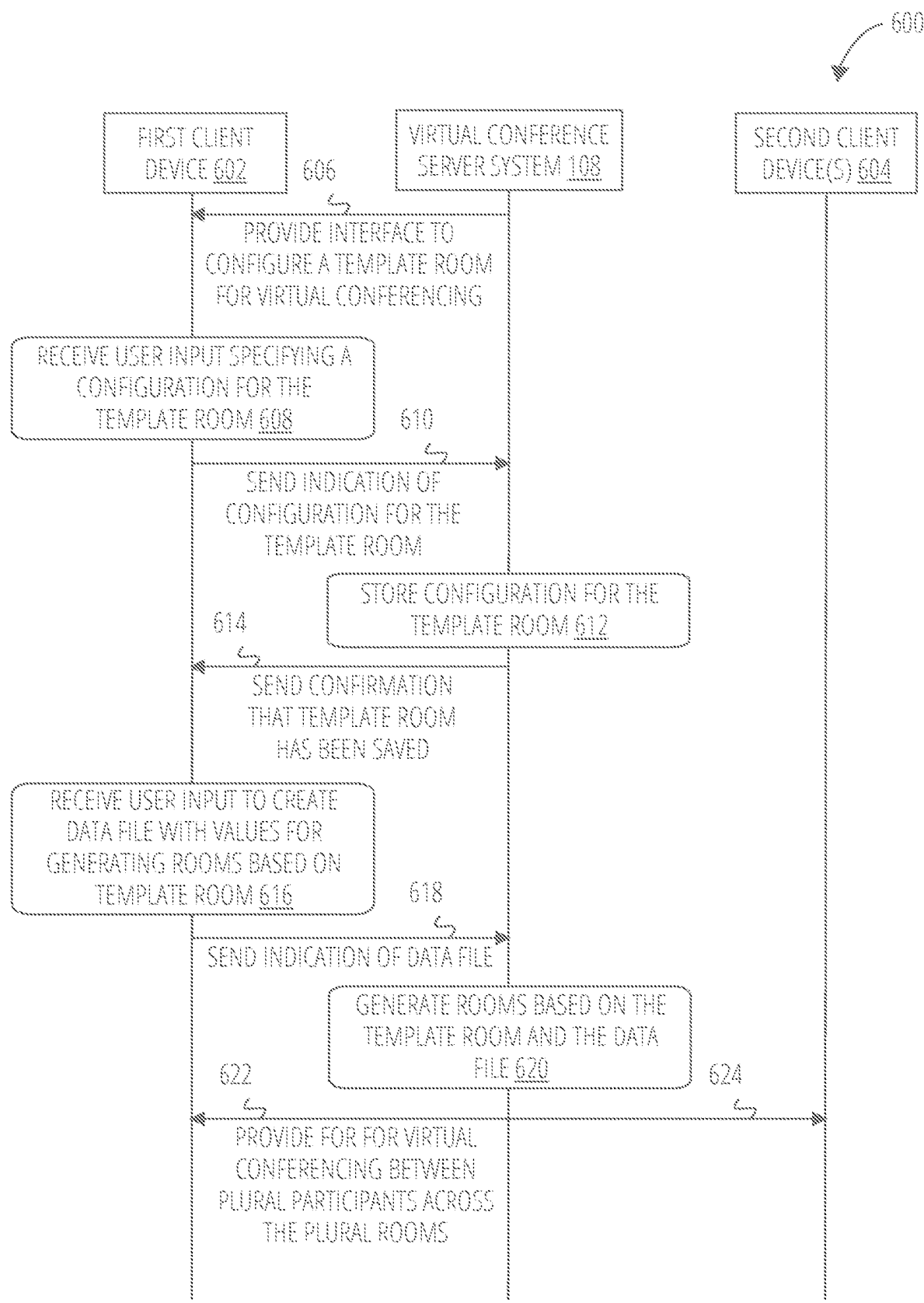
FIG. 6 is an interaction diagram illustrating a process for providing template rooms within a virtual conferencing system, in accordance with some example embodiments.

FIG. 6 is an interaction diagram illustrating a process 600 for providing template rooms within a virtual conferencing system, in accordance with some example embodiments. For explanatory purposes, the process 600 is described herein with reference to a first client device 602, second client device(s) 604, and the virtual conference server system 108. Each of the first client device 602 and the second client device(s) 604 may correspond to a respective client device 102. The process 600 is not limited to the first client device 602, the second client device(s) 604 and the virtual conference server system 108. Moreover, one or more blocks (or operations) of the process 600 may be performed by one or more other components of the first client device 602, the second client device(s) 604 or the virtual conference server system 108, and/or by other suitable devices. Further for explanatory purposes, the blocks (or operations) of the process 600 are described herein as occurring in serial, or linearly. However, multiple blocks (or operations) of the process 600 may occur in parallel or concurrently. In addition, the blocks (or operations) of the process 600 need not be performed in the order shown and/or one or more blocks (or operations) of the process 600 need not be performed and/or can be replaced by other operations. The process 600 may be terminated when its operations are completed. In addition, the process 600 may correspond to a method, a procedure, an algorithm, etc.

Each of the first client device 602 and the second client device(s) 604 have instances of the virtual conference client 104 installed thereon. In the example of FIG. 6, the first client device 602 and the second client device(s) 604 are associated with a respective first participant and a second participant of the virtual conference server system 108. For example, the first participant may be associated with a first user account of the virtual conference server system 108, and the second participant may be associated with a second user account of the virtual conference server system 108.

As noted above, the first and second participants are identifiable by the virtual conference server system 108 based on unique identifiers (e.g., email addresses, telephone numbers) associated with respective user accounts for the first and second participants. In one or more embodiments, the virtual conference server system 108 implements and/or works in conjunction with a social network server 122 which is configured to identify contacts with which a particular user has relationships. For example, the first and second participants may be contacts with respect to the virtual conference server system 108.

As described herein, the virtual conferencing system 100 provides for an administrator (e.g., the first participant) to generate multiple rooms based on a single template room and a data file. In doing so, the virtual conference server system 108 provides an interface to configure a template room for virtual conferencing. The user may initially configure a template room via the interface. The user may then create or otherwise edit a data file with values for generating a plurality of rooms (e.g., tens of rooms, hundreds of rooms) based on the template room.

A template room corresponds to a type of room which is configurable to be replicated, for example, based on values included in a data file as described herein. The template room may be made available via the menu interface 402 of FIG. 4. For example, the menu interface 402 may provide an element (e.g., a "room schema") for configuring a template room. In one or more embodiments, a template room may include elements and/or shapes described above with respect to the element category of the menu interface 402 in FIG. 4. For example, a template room may be configured to include element(s) such as: an action button, analog clock, audience question board, backpack item, breakout button, chat, closed caption display, closed caption input, countdown, clock, digital clock, doorbell, double-sided image, feedback, image, multiuser video chat, music, participant audio mixer, participant count, participant video element (e.g., single or multiple), picture strip, poll, random source, room preview, scheduled time, sound effect, stopwatch, take picture, text, timer, user search, video, waiting list, web media, website, or a shape (e.g., circle, rectangle, triangle).

Moreover, the element properties interface 406 includes various fields for setting configuration properties for the template room and its individual elements. As noted above, the user may specify, via the element properties interface 406, properties including: title/name, opacity, color/gradient, style, layout, borders/corners, shadows, interaction (e.g., to what extent participant(s) may delete, modify, resize the element), filtering, full screen status, conditions, accessibility and actions for the template room and elements therein.

Thus, the virtual conference server system 108 provides an interface for a user (e.g., the first participant) to configure a template room for virtual conferencing (operation 606). In the example of FIG. 6, the first client device 602 receives user input, via the interface, for specifying a configuration for a template room (block 608). In one or more embodiments, the first participant designs the room from scratch (e.g., based on a blank room template), and adds and configures room elements as described above. In alternate embodiments, the virtual conference server system 108 may store predesigned rooms, and the first participant may start with the predesigned room, and make updates to the predesigned room in order to specify the configuration for the template room with respect to block 608.

The first client device 602 sends an indication of the configuration for the template room to the virtual conference server system 108 (operation 610). The virtual conference server system 108 stores the configuration for the template room (block 612). For example, the virtual conference server system 108 provides for storing general room properties and/or properties for elements of the template room within the rooms table 310 of the database 126, in association with the template room. At operation 614, the virtual conference server system 108 sends a confirmation that the template room has been saved, and is available for generating multiple rooms in association with a data file.

The virtual conference server system 108 is configured generate multiple rooms from the template room, but customized based on data values included within a data file. Each generated room is a copy of the template room that has been updated to reflect the values in the data file.

In one or more embodiments, the data file is a comma-separated values (CSV) file. The CSV includes a header for defining updates to the template room. As discussed further below with respect to FIG. 7, the header includes a first column called "title." The header may include other column headers having the format element_title [property_name], for supplementing the template room with text, image data (e.g., pictures, videos) and/or other content. In one or more embodiments, the property_name field may correspond to one or more of the above-listed elements provided by the element category of the menu interface 402.

In addition, the virtual conference server system 108 provides for referencing values from another room defined inside of the data file. For example, to link to a specific room using CSV data, values with the form ${room:RoomTitle}[id] will select the id value from the room with title RoomTitle.

Thus, at block 616, the first client device 602 receives user input (e.g., via the first participant) to create or otherwise update a data file with values for generating rooms based on the template room. In one or more embodiments, the first participant may create/open the data file (e.g., as a text file) and add values for generating multiple rooms based on the values in the data file. The first client device 602 sends an indication of the data file to the virtual conference server system 108.

In response, the virtual conference server system 108 generates rooms based on the template room and above-noted values (e.g., title, additional text and/or image data) extracted from the data file (block 620). In this regard, the virtual conference server system 108 may provide an interface for associating the data file with a particular template room. In one or more embodiments, the generated rooms are added to the room list interface 410 of the virtual space design interface 204.

At operation 622-624, the virtual conference server system 108 provides for virtual conferencing between plural participants across the plural rooms (e.g., as defined by the values within the data file). For example, the generated rooms are added to the room list interface 504 of the virtual space navigation interface 208. During virtual conferencing, each of the generated rooms corresponds to the template room, but is supplemented and/or customized with content (e.g., text and/or image elements) based on the respective values included in the data file.

Thus, the virtual conferencing system 100 as described herein allows a user (e.g., administrator) to generate multiple rooms based on a single template room and a data file. In doing so, the virtual conference server system 108 provides an interface to configure a template room for virtual conferencing. The user may initially configure a template room via the interface. The user may then create or otherwise edit a data file with values for generating a plurality of rooms (e.g., tens of rooms, hundreds of rooms) based on the template room. The data file may include user-entered values for supplementing or otherwise customizing the template room, such that the multiple rooms vary in some aspects.

By virtue of allowing a user to define a template room and create a data file in this manner, it is possible for the user to create multiple rooms automatically in a batched fashion. In addition, the configuration of the multiple room may be more consistent across the virtual space. Without allowing the user (e.g., administrator) to configure generate multiple rooms via the data file, the user may be required to perform redundant actions (e.g., copying and pasting) to manually create each room. The virtual conferencing system 100 facilitates creation of virtual conferencing environments, thereby saving time for the user, and reducing computational resources/processing power for the virtual conferencing system 100.

Figure 7:
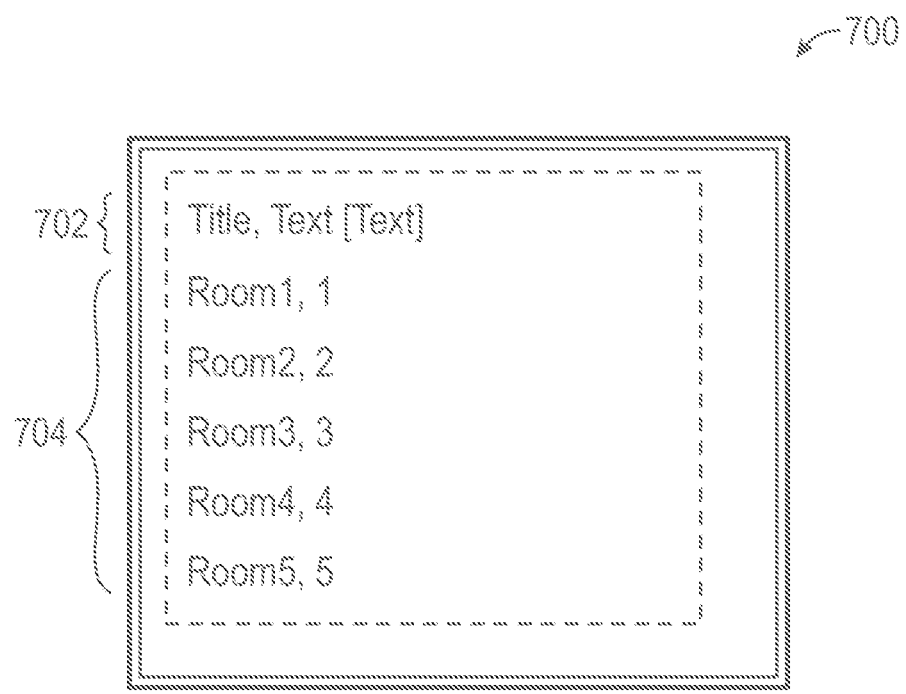
FIG. 7 illustrates an example data file with values for generating multiple rooms from a template room, in accordance with some example embodiments.

FIG. 7 illustrates an example data file 700 (e.g., the contents thereof) with values for generating multiple rooms from a template room, in accordance with some example embodiments. As noted above, the data file 700 is usable by the virtual conference server virtual conferencing system 100 to generate multiple rooms from a particular template room selected by the user, with customizations based on data values included in the data file 700. Each generated room is a copy of the template room that is updated to reflect the values in the data file.

The example of FIG. 7 depicts the data file 700 as a CSV file. The data file 700 includes a header 702 which includes separate columns for each user-selectable value. The first column is a "title," which corresponds to the respective title of the room for display within the room. The second column of the header 702 has the format element_title [property_name]. In the example of FIG. 7, the element_title is "text" and the property_name is "text."

The data file 700 further includes room values 704, which appear as rows within the data file 700. For example, each row includes values for generating a respective room within the virtual space. In the example of FIG. 7, the room values 704 specify to generate five rooms based on the template room. Each of the five rooms has a respective value for the above-noted "title" and element_title [property_name]. The first room's title is set to "Room1" and ha the "text" field set to the value of "text." The second through fifth room's have respective titles and text field values from "2" through "5."

Figure 8:
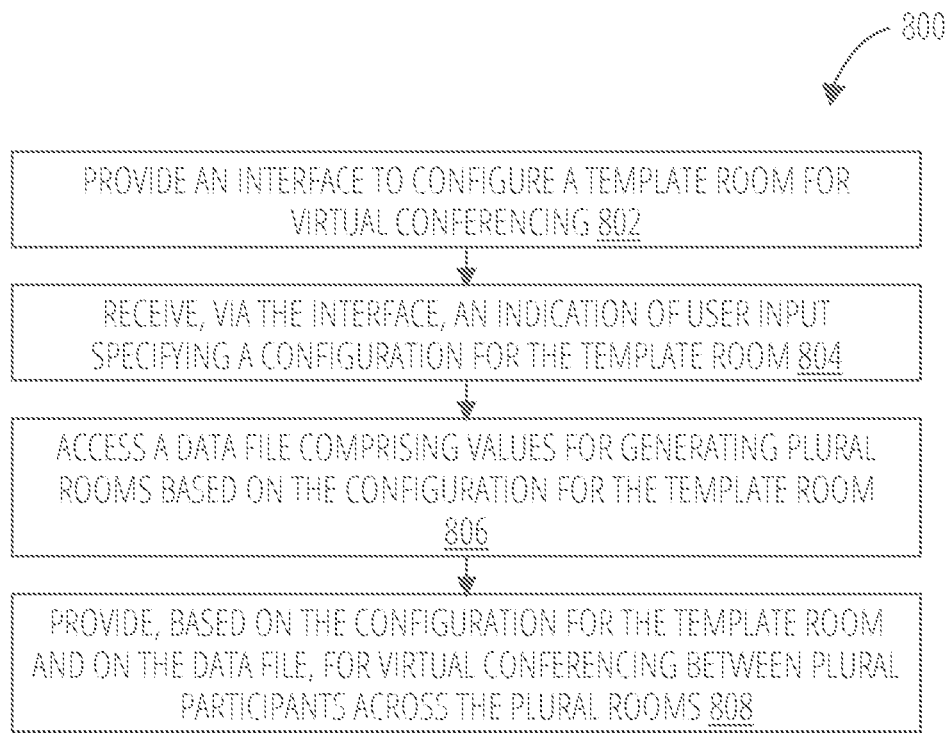
FIG. 8 is a flowchart illustrating a process for providing template rooms within a virtual conferencing system, in accordance with some example embodiments.

FIG. 8 is a flowchart illustrating a process 800 for providing template rooms within a virtual conferencing system, in accordance with some example embodiments. For explanatory purposes, the process 800 is primarily described herein with reference to the first client device 602, the second client device(s) 604 and the virtual conference server system 108 of FIG. 1 and FIG. 2. However, one or more blocks (or operations) of the process 800 may be performed by one or more other components, and/or by other suitable devices. Further for explanatory purposes, the blocks (or operations) of the process 800 are described herein as occurring in serial, or linearly. However, multiple blocks (or operations) of the process 800 may occur in parallel or concurrently. In addition, the blocks (or operations) of the process 800 need not be performed in the order shown and/or one or more blocks (or operations) of the process 800 need not be performed and/or can be replaced by other operations. The process 800 may be terminated when its operations are completed. In addition, the process 800 may correspond to a method, a procedure, an algorithm, etc.

The virtual conference server system 108 provides an interface to configure a template room for virtual conferencing (block 802). The virtual conference server system 108 receives, via the interface, an indication of user input specifying a configuration for the template room (block 804).

The virtual conference server system 108 accesses a data file comprising values for generating plural rooms based on the configuration for the template room (block 806). The data file may be a comma-separated values (CSV) file.

The values may be user-specified within the data file. The values may include a title and at least one property for each of the plural rooms. For a first of the plural rooms, the title or the at least one property may be a reference to a corresponding title or to a corresponding at least one property from a second of the plural rooms. The at least one property may include text or image data.

The virtual conference server system 108 provides, based on the configuration for the template room and on the data file, for virtual conferencing between plural participants across the plural rooms (block 808). The virtual conference server system 108 may provide, for each of the plural participants, display of a participant video element which corresponds to the participant and which includes a video feed for the participant.

Figure 9:
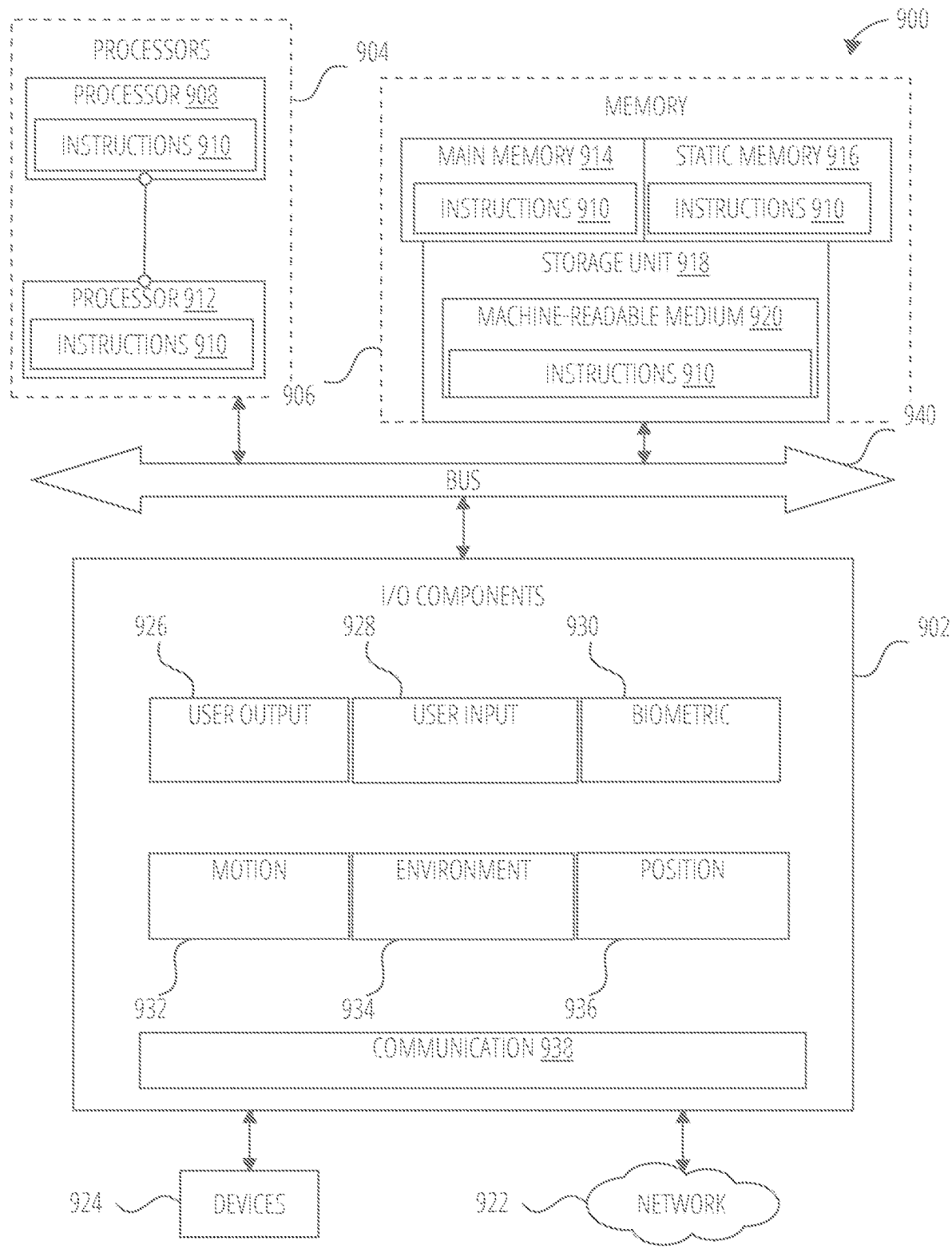
FIG. 9 is a diagrammatic representation of a machine in the form of a computer system within which a set of instructions may be executed for causing the machine to perform any one or more of the methodologies discussed herein, in accordance with some examples.

FIG. 9 is a diagrammatic representation of the machine 900 within which instructions 910 (e.g., software, a program, an application, an applet, an app, or other executable code) for causing the machine 900 to perform any one or more of the methodologies discussed herein may be executed. For example, the instructions 910 may cause the machine 900 to execute any one or more of the methods described herein. The instructions 910 transform the general, non-programmed machine 900 into a particular machine 900 programmed to carry out the described and illustrated functions in the manner described. The machine 900 may operate as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 910, sequentially or otherwise, that specify actions to be taken by the machine 900. Further, while only a single machine 900 is illustrated, the term "machine" shall also be taken to include a collection of machines that individually or jointly execute the instructions 910 to perform any one or more of the methodologies discussed herein. The machine 900, for example, may comprise the client device 102 or any one of a number of server devices forming part of the virtual conference server system 108. In some examples, the machine 900 may also comprise both client and server systems, with certain operations of a particular method or algorithm being performed on the server-side and with certain operations of the particular method or algorithm being performed on the client-side.

The machine 900 may include processors 904, memory 906, and input/output I/O components 902, which may be configured to communicate with each other via a bus 940. In an example, the processors 904 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 908 and a processor 912 that execute the instructions 910. The term "processor" is intended to include multi-core processors that may comprise two or more independent processors (sometimes referred to as "cores") that may execute instructions contemporaneously. Although FIG. 9 shows multiple processors 904, the machine 900 may include a single processor with a single-core, a single processor with multiple cores (e.g., a multi-core processor), multiple processors with a single core, multiple processors with multiples cores, or any combination thereof.

The memory 906 includes a main memory 914, a static memory 916, and a storage unit 918, both accessible to the processors 904 via the bus 940. The main memory 906, the static memory 916, and storage unit 918 store the instructions 910 embodying any one or more of the methodologies or functions described herein. The instructions 910 may also reside, completely or partially, within the main memory 914, within the static memory 916, within machine-readable medium 920 within the storage unit 918, within at least one of the processors 904 (e.g., within the Processor's cache memory), or any suitable combination thereof, during execution thereof by the machine 900.

The I/O components 902 may include a wide variety of components to receive input, provide output, produce output, transmit information, exchange information, capture measurements, and so on. The specific I/O components 902 that are included in a particular machine will depend on the type of machine. For example, portable machines such as mobile phones may include a touch input device or other such input mechanisms, while a headless server machine will likely not include such a touch input device. It will be appreciated that the I/O components 902 may include many other components that are not shown in FIG. 9. In various examples, the I/O components 902 may include user output components 926 and user input components 928. The user output components 926 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 928 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 902 may include biometric components 930, motion components 932, environmental components 934, or position components 936, among a wide array of other components. For example, the biometric components 930 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 932 include acceleration sensor components (e.g., accelerometer), gravitation sensor components, rotation sensor components (e.g., gyroscope).

The environmental components 934 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the client device 102 may have a camera system comprising, for example, front cameras on a front surface of the client device 102 and rear cameras on a rear surface of the client device 102. The front cameras may, for example, be used to capture still images and video of a user of the client device 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the client device 102 may also include a 360° camera for capturing 360° photographs and videos.

Further, the camera system of a client device 102 may include dual rear cameras (e.g., a primary camera as well as a depth-sensing camera), or even triple, quad or penta rear camera configurations on the front and rear sides of the client device 102. These multiple cameras systems may include a wide camera, an ultra-wide camera, a telephoto camera, a macro camera and a depth sensor, for example.

The position components 936 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 902 further include communication components 938 operable to couple the machine 900 to a network 922 or devices 924 via respective coupling or connections. For example, the communication components 938 may include a network interface Component or another suitable device to interface with the network 922. In further examples, the communication components 938 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 924 may be another machine or any of a wide variety of peripheral devices (e.g., a peripheral device coupled via a USB).

Moreover, the communication components 938 may detect identifiers or include components operable to detect identifiers. For example, the communication components 938 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 938, such as location via Internet Protocol (IP) geolocation, location via Wi-Fi® signal triangulation, location via detecting an NFC beacon signal that may indicate a particular location, and so forth.

The various memories (e.g., main memory 914, static memory 916, and memory of the processors 904) and storage unit 918 may store one or more sets of instructions and data structures (e.g., software) embodying or used by any one or more of the methodologies or functions described herein. These instructions (e.g., the instructions 910), when executed by processors 904, cause various operations to implement the disclosed examples.

The instructions 910 may be transmitted or received over the network 922, using a transmission medium, via a network interface device (e.g., a network interface component included in the communication components 938) and using any one of several well-known transfer protocols (e.g., hypertext transfer protocol (HTTP)). Similarly, the instructions 910 may be transmitted or received using a transmission medium via a coupling (e.g., a peer-to-peer coupling) to the devices 924.

Figure 10:
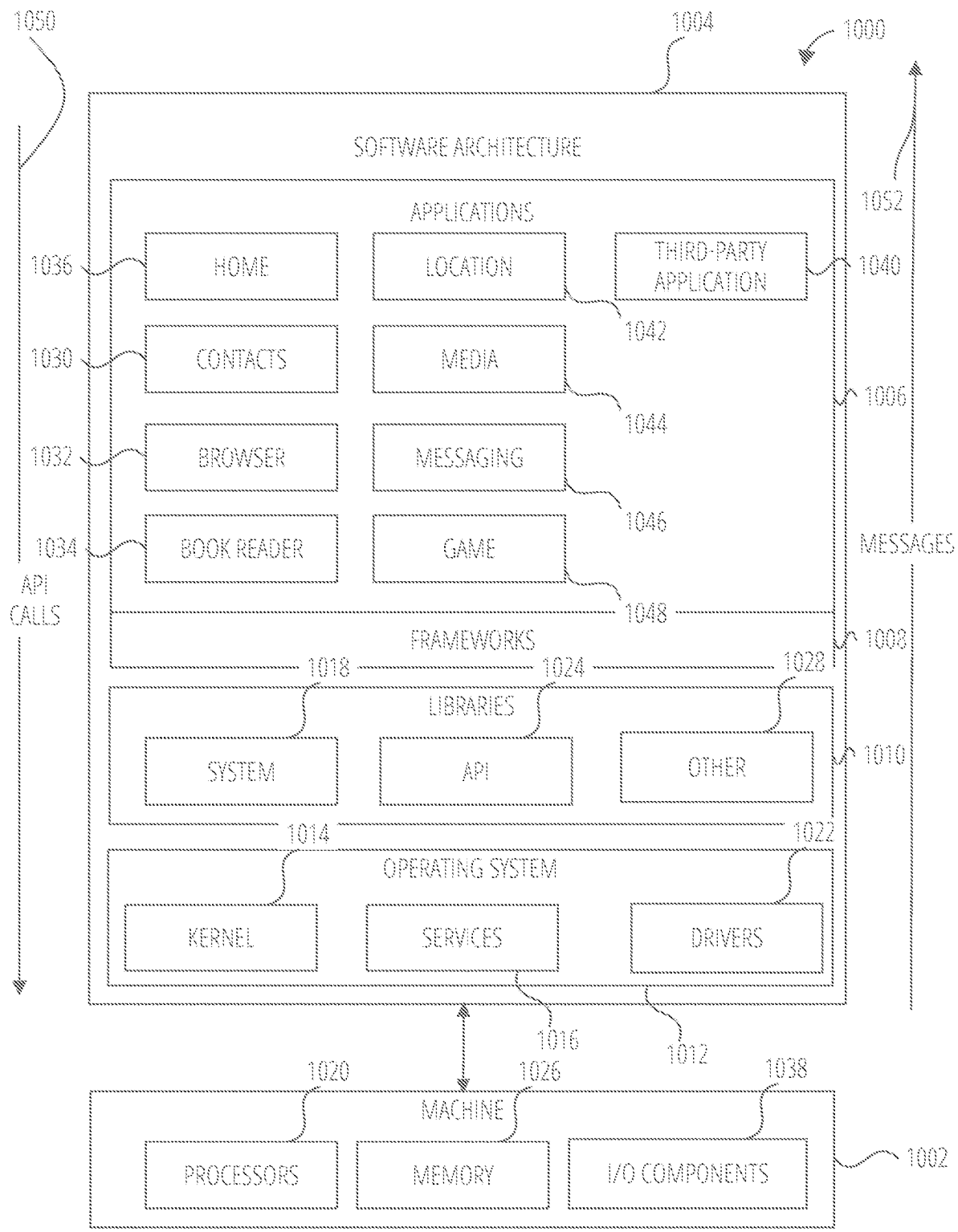
FIG. 10 is a block diagram showing a software architecture within which examples may be implemented.

FIG. 10 is a block diagram 1000 illustrating a software architecture 1004, which can be installed on any one or more of the devices described herein. The software architecture 1004 is supported by hardware such as a machine 1002 that includes processors 1020, memory 1026, and I/O components 1038. In this example, the software architecture 1004 can be conceptualized as a stack of layers, where each layer provides a particular functionality. The software architecture 1004 includes layers such as an operating system 1012, libraries 1010, frameworks 1008, and applications 1006. Operationally, the applications 1006 invoke API calls 1050 through the software stack and receive messages 1052 in response to the API calls 1050.

The operating system 1012 manages hardware resources and provides common services. The operating system 1012 includes, for example, a kernel 1014, services 1016, and drivers 1022. The kernel 1014 acts as an abstraction layer between the hardware and the other software layers. For example, the kernel 1014 provides memory management, processor management (e.g., scheduling), component management, networking, and security settings, among other functionality. The services 1016 can provide other common services for the other software layers. The drivers 1022 are responsible for controlling or interfacing with the underlying hardware. For instance, the drivers 1022 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1010 provide a common low-level infrastructure used by the applications 1006. The libraries 1010 can include system libraries 1018 (e.g., C standard library) that provide functions such as memory allocation functions, string manipulation functions, mathematic functions, and the like. In addition, the libraries 1010 can include API libraries 1024 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1010 can also include a wide variety of other libraries 1028 to provide many other APIs to the applications 1006.

The frameworks 1008 provide a common high-level infrastructure that is used by the applications 1006. For example, the frameworks 1008 provide various graphical user interface (GUI) functions, high-level resource management, and high-level location services. The frameworks 1008 can provide a broad spectrum of other APIs that can be used by the applications 1006, some of which may be specific to a particular operating system or platform.

In an example, the applications 1006 may include a home application 1036, a contacts application 1030, a browser application 1032, a book reader application 1034, a location application 1042, a media application 1044, a messaging application 1046, a game application 1048, and a broad assortment of other applications such as a third-party application 1040. The applications 1006 are programs that execute functions defined in the programs. Various programming languages can be employed to create one or more of the applications 1006, structured in a variety of manners, such as object-oriented programming languages (e.g., Objective-C, Java, or C++) or procedural programming languages (e.g., C or assembly language). In a specific example, the third-party application 1040 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 1040 can invoke the API calls 1050 provided by the operating system 1012 to facilitate functionality described herein.

Glossary

"Carrier signal" refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

"Client device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi®& network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices, magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

What is claimed is:

1. A method, comprising:
providing an interface to configure a template room for virtual conferencing;
receiving, via the interface, an indication of input provided by a user specifying elements for the template room and properties of the elements;
providing the user with access to a data file for generating plural rooms based on the elements for the template room and the properties of the elements, such that the data file is manually opened and updated by the user with text-based values, the data file being organized to include a separate entry with respective text-based values to generate each room of the plural rooms;
accessing the data file to determine the text-based values as manually updated by the user; and
providing, based on the elements for the template room, on the properties of the elements and on the text-based values, for virtual conferencing between plural participants across the plural rooms.

2. The method of claim 1, wherein the separate entry with respective values comprises a title and at least one property for generating each room of the plural rooms.

3. The method of claim 2, wherein the plural rooms comprise a first room and a second room, and
wherein for the second room, the title or the at least one property is predefined text indicating to reference a corresponding title or a corresponding at least one property from the first room.

4. The method of claim 2, wherein the at least one property comprises text.

5. The method of claim 2, wherein the at least one property comprises image data.

6. The method of claim 1, wherein the data file is a comma-separated values (CSV) file.

7. The method of claim 1, further comprising:
providing, for each of the plural participants, display of a participant video element which corresponds to the participant and which includes a video feed for the participant.

8. The method of claim 1, wherein the elements of the room, as specified by the user via the interface, include at least one of an action button, analog clock, audience question board, backpack item, breakout button, chat, closed caption display, closed caption input, countdown, clock, digital clock, doorbell, double-sided image, feedback, image, multiuser video chat, music, participant audio mixer, participant count, participant video element, picture strip, poll, random source, room preview, scheduled time, sound effect, stopwatch, take picture, text, timer, user search, video, waiting list, web media, website, or a shape.

9. The method of claim 8, wherein the properties of the elements, as specified by the user via the interface include at least one of a title/name, opacity, color/gradient, style, layout, borders/corners, shadows, interaction, filtering, full screen status, conditions, accessibility or actions.

10. A system comprising:
a processor; and
a memory storing instructions that, when executed by the processor, configure the processor to perform operations comprising:
providing an interface to configure a template room for virtual conferencing;
receiving, via the interface, an indication of input provided by a user specifying elements for the template room and properties of the elements;

providing the user with access to a data file for generating plural rooms based on the elements for the template room and the properties of the elements, such that the data file is manually opened and updated by the user with text-based values, the data file being organized to include a separate entry with respective text-based values to generate each room of the plural rooms;

accessing the data file to determine the text-based values as manually updated by the user; and providing, based on the elements for the template room, on the properties of the elements and on the text-based values, for virtual conferencing between plural participants across the plural rooms.

11. The system of claim 10, wherein the separate entry with respective values comprises a title and at least one property for generating each room of the plural rooms.

12. The system of claim 11, wherein the plural rooms comprise a first room and a second room, and wherein for the second room, the title or the at least one property is predefined text indicating to reference a corresponding title or a corresponding at least one property from the first room.

13. The system of claim 11, wherein the at least one property comprises text.

14. The system of claim 11, wherein the at least one property comprises image data.

15. The system of claim 10, wherein the data file is a comma-separated values (CSV) file.

16. The system of claim 10, the operations further comprising:

providing, for each of the plural participants, display of a participant video element which corresponds to the participant and which includes a video feed for the participant.

17. A non-transitory computer-readable storage medium, the computer-readable storage medium including instructions that when executed by a computer, cause the computer to perform operations comprising:

providing an interface to configure a template room for virtual conferencing;

receiving, via the interface, an indication of input provided by a user specifying elements for the template room and properties of the elements;

providing the user with to accessing a data file for generating plural rooms based on the elements for the template room and the properties of the elements, such that the data file is manually opened and updated by the user with text-based values, the data file being organized to include a separate entry with respective text-based values to generate each room of the plural rooms;

accessing the data file to determine the text-based values as manually updated by the user; and providing, based on the elements for the template room, on the properties of the elements and on the text-based values, for virtual conferencing between plural participants across the plural rooms.

18. The computer-readable medium of claim 17, wherein the separate entry with respective values comprises a title and at least one property for generating each room of the plural rooms.

19. The computer-readable medium of claim 18, wherein the plural rooms comprise a first room and a second room, and wherein for the second room, the title or the at least one property is predefined text indicating to reference a corresponding title or a corresponding at least one property from the first room.

* * * * *

UNITED STATES PATENT AND TRADEMARK OFFICE
CERTIFICATE OF CORRECTION

Page 1 of 1

PATENT NO. : 12,244,966 B2
APPLICATION NO. : 17/956549
DATED : March 4, 2025
INVENTOR(S) : Lin et al.

It is certified that error appears in the above-identified patent and that said Letters Patent is hereby corrected as shown below:

In the Claims

In Column 24, Line 10, in Claim 17, delete "to accessing" and insert --access to-- therefor Signed and Sealed this
Thirteenth Day of May, 2025

Coke Morgan Stewart
*Acting Director of the United States Patent and Trademark Office*